US012227518B2

United States Patent
Srinivasan et al.

(10) Patent No.: US 12,227,518 B2
(45) Date of Patent: Feb. 18, 2025

(54) CRYSTALLINE POLYMORPHS OF SODIUM (4R,12AS)-9-{[(2,4-DIFLUOROPHENYL) METHYL]CARBAMOYL}-4-METHYL-6,8-DIOXO-3,4,6,8,12,12A-HEXAHYDRO-2H-PYRIDO [1',2':4,5]PYRAZINO[2,1-B][1,3] OXAZIN-7-OLATE AND PROCESS FOR PREPARATION THEREOF

(71) Applicant: MSN LABORATORIES PRIVATE LIMITED, R&D CENTER, Telangan (IN)

(72) Inventors: Thirumalai Rajan Srinivasan, Hyderabad (IN); Eswaraiah Sajja, Hyderabad (IN); Rajeshwar Reddy Sagyam, Hyderabad (IN); Srinivasulu Ragineni, Hyderabad (IN); Venkata Narasayya Saladi, Hyderabad (IN)

(73) Assignee: MSN LABORATORIES PRIVATE LIMITED, R&D CENTER, Telangana (IN)

( * ) Notice: Subject to any disclaimer, the term of this patent is extended or adjusted under 35 U.S.C. 154(b) by 814 days.

(21) Appl. No.: 17/428,745

(22) PCT Filed: Feb. 4, 2020

(86) PCT No.: PCT/IN2020/050116
§ 371 (c)(1),
(2) Date: Aug. 5, 2021

(87) PCT Pub. No.: WO2020/161742
PCT Pub. Date: Aug. 13, 2020

(65) Prior Publication Data
US 2022/0112212 A1     Apr. 14, 2022

(30) Foreign Application Priority Data

Feb. 5, 2019   (IN) .............................. 201941004608
May 7, 2019   (IN) .............................. 201941018234

(51) Int. Cl.
*C07D 498/14*   (2006.01)
(52) U.S. Cl.
CPC ........ *C07D 498/14* (2013.01); *C07B 2200/13* (2013.01)
(58) Field of Classification Search
CPC .................. C07D 498/14; C07B 2200/13
See application file for complete search history.

(56) References Cited

U.S. PATENT DOCUMENTS

2015/0231079 A1* 8/2015 Malhotra ............. A61K 9/2013
514/230.2
2017/0217987 A1* 8/2017 Hotter ..................... A61P 31/18

FOREIGN PATENT DOCUMENTS

WO   WO 2015118460 A1   8/2015
WO   WO 2016016279 A1   2/2016

OTHER PUBLICATIONS

Search Steategy dated Aug. 13, 2020 in the file history of the corresponding international application.
International Search Report dated Aug. 13, 2020.
Written Opinion of the International Searching Authority dated Aug. 13, 2020.
Caira M, R., "Crystalline Polymorphisms of Organic Compounds," Topics in Current Chemistry, Springer, Berlin, DE, vol. 198, Jan. 1, 1998, pp. 163-208.

* cited by examiner

*Primary Examiner* — Timothy R Rozof
(74) *Attorney, Agent, or Firm* — IP PUNDIT LLC (57) ABSTRACT

The present invention relates to novel crystalline polymorphs of sodium (4R,12aS)-9-{[(2,4-difluorophenyl) methyl]carbamoyl}-4-methyl-6,8-dioxo-3,4,6,8,12,12a-hexahydro-2H-pyrido[1',2':4,5] pyrazino[2,1-b] [1,3] oxazin-7-olate represented by the following structural formula-1a and process for their preparation.
The present invention further relates to novel solvated forms of sodium (4R,12aS)-9-{[(2,4-difluoro phenyl) methyl] carbamoyl}-4-methyl-6,8-dioxo-3,4,6,8,12,12a-hexahydro-2H-pyrido[1',2':4,5] pyrazino[2,1-b][1,3] oxazin-7-olate compound of formula-1a and process for their preparation.

Formula-1a

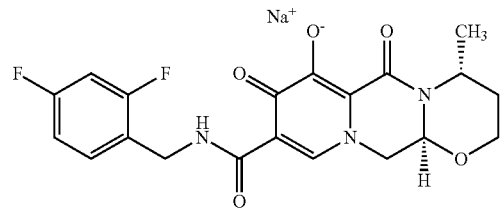

16 Claims, 4 Drawing Sheets

CRYSTALLINE POLYMORPHS OF SODIUM (4R,12AS)-9-{[(2,4-DIFLUOROPHENYL) METHYL]CARBAMOYL}-4-METHYL-6,8-DIOXO-3,4,6,8,12,12A-HEXAHYDRO-2H-PYRIDO [1',2':4,5]PYRAZINO[2,1-B][1,3] OXAZIN-7-OLATE AND PROCESS FOR PREPARATION THEREOF

RELATED APPLICATIONS

This application is a U.S. National Stage application of PCT International Patent Application Number PCT/IN2020/050116, which was filed on Feb. 5, 2020, which claims the benefit of priority of the Indian patent applications 201941004608, filed on Feb. 5, 2019, and 201941018234, filed on May 7, 2019, the disclosures of all of which are incorporated herein by reference.

FIELD OF THE INVENTION

The present invention provides novel crystalline polymorphs of sodium (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate represented by the following structural formula-1a, its solvates and process for preparation thereof.

Formula-1a

BACKGROUND OF THE INVENTION

Sodium (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate is commonly known as Dolutegravir sodium and was approved in US under the brand name TIVICAY® which is indicated for the treatment of human immunodeficiency virus (HIV) infection in combination with other antiretroviral agents.

(4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-ol (commonly known as Dolutegravir), its salts and process for their preparation is first disclosed in U.S. Pat. No. 8,129,385B2.

U.S. Pat. No. 9,242,986B2 patent describes two crystalline polymorphs of sodium (4R,12aS)-9-{[(2,4-difluorophenyl)methyl]carbamoyl}-4-methyl-6,8-dioxo-3,4,6,8,12,12a-hexahydro-2H-pyrido[1',2': 4,5]pyrazino[2,1-b][1,3]oxazin-7-olate.

U.S. Pat. No. 9,206,197B2 patent describes amorphous form of sodium (4R,12aS)-9-{[(2,4-difluorophenyl)methyl]carbamoyl}-4-methyl-6,8-dioxo-3,4,6,8,12,12a-hexahydro-2H-pyrido[1',2': 4,5]pyrazino[2,1-b][1,3]oxazin-7-olate.

WO2015092752A1 patent publication describes NMP solvate of sodium (4R,12aS)-9-{[(2,4-difluorophenyl)methyl]carbamoyl}-4-methyl-6,8-dioxo-3,4,6,8,12,12a-hexahydro-2H-pyrido[1',2': 4,5]pyrazino[2,1-b][1,3]oxazin-7-olate.

WO2015118460A1 patent publication describes crystalline form-M2, form-M3, form-M4 of sodium (4R,12aS)-9-{[(2,4-difluorophenyl)methyl] carbamoyl}-4-methyl-6,8-dioxo-3,4,6,8,12,12a-hexahydro-2H-pyrido[1',2':4,5]pyrazino[2,1-b][1,3]oxazin-7-olate.

WO2015139591A1 patent publication describes crystalline form-A, B, C, D, E of sodium (4R,12aS)-9-{[(2,4-difluorophenyl)methyl]carbamoyl}-4-methyl-6,8-dioxo-3,4,6,8,12,12a-hexahydro-2H-pyrido[1',2': 4,5]pyrazino[2,1-b][1,3]oxazin-7-olate.

WO2016102078A1 patent publication describes 1,2-propylene glycol solvate of sodium (4R,12aS)-9-{[(2,4-difluorophenyl)methyl]carbamoyl}-4-methyl-6,8-dioxo-3,4,6,8,12,12a-hexahydro-2H-pyrido[1',2': 4,5]pyrazino[2,1-b][1,3]oxazin-7-olate.

WO2017029642A2 patent publication describes crystalline form-L9, L10, L11 and L12 of sodium (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate.

WO2017208105A1 patent publication describes crystalline form-A of sodium (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate.

Still, there is a need in the art to develop novel crystalline polymorph of sodium (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate which is suitable for the preparation of various pharmaceutical compositions.

BRIEF DESCRIPTION OF THE INVENTION

The present invention provides novel crystalline polymorph of sodium (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate compound of formula-1a, which is herein after designated as crystalline form-S and process for its preparation.

The present invention further provides novel crystalline polymorph of compound of formula-1a, which is herein after designated as crystalline form-N and process for its preparation.

The present invention further provides crystalline 1,3-butane diol solvate of compound of formula-1a and process for its preparation.

The present invention further provides crystalline benzyl alcohol solvate of compound of formula-1a and process for its preparation.

The present invention further provides novel crystalline polymorph of compound of formula-1a, which is herein after designated as crystalline form-L and process for its preparation.

DETAILED DESCRIPTION OF THE INVENTION

The term "suitable solvent" used in the present invention refers to "hydrocarbon solvents" such as n-pentane, n-hexane, n-heptane, cyclohexane, pet ether, benzene, toluene, xylene and the like; "ether solvents" such as dimethyl ether, diethyl ether, diisopropyl ether, methyl tert-butyl ether, 1,2-dimethoxyethane, tetrahydrofuran, 1,4-dioxane and the like; "ester solvents" such as methyl acetate, ethyl acetate, n-propyl acetate, isopropyl acetate, n-butyl acetate, isobutyl acetate, tert-butyl acetate and the like; "polar-aprotic solvents" such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcohol solvents" such as methanol, ethanol, n-propanol, iso-propanol (isopropyl alcohol), n-butanol, iso-butanol, t-butanol, ethane-1,2-diol, propane-1,2-diol and the like; "polar solvents" such as water; formic acid, acetic acid or mixture of any of the aforementioned solvents.

The first embodiment of the present invention provides a crystalline polymorph of compound of formula-1a characterized by its PXRD pattern having peaks at about 6.4, 11.6, 14.2 and 16.5±0.2° of 2θ.

Figure 1:
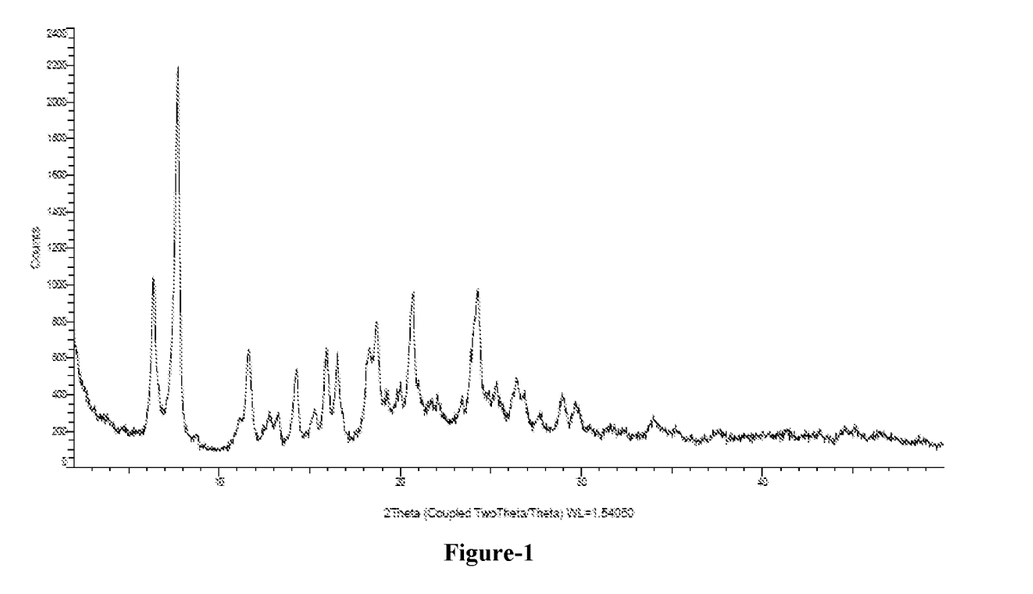
FIG. 1: Illustrates the PXRD pattern of crystalline form-S of compound of formula-1a FIG. 2: Illustrates the PXRD pattern of crystalline form-N of compound of formula-1a FIG. 3: Illustrates the PXRD pattern of crystalline 1,3-butane diol solvate of compound of formula-1a FIG. 4: Illustrates the PXRD pattern of crystalline benzyl alcohol solvate of compound of formula-1a FIG. 5: Illustrates the PXRD pattern of compound of formula-1a obtained according to example-5 (before drying)

In one aspect of the first embodiment of the present invention, the above crystalline polymorph is further characterized by;
a) its PXRD pattern having peaks at about 7.7, 12.8, 13.2, 15.2, 15.9, 18.3, 18.6, 19.9, 20.6, 24.2, 25.3, 26.4, 28.9 and 29.7±0.2° of 2θ, and/or
b) its PXRD pattern as illustrated in FIG. 1.

Figure 6:
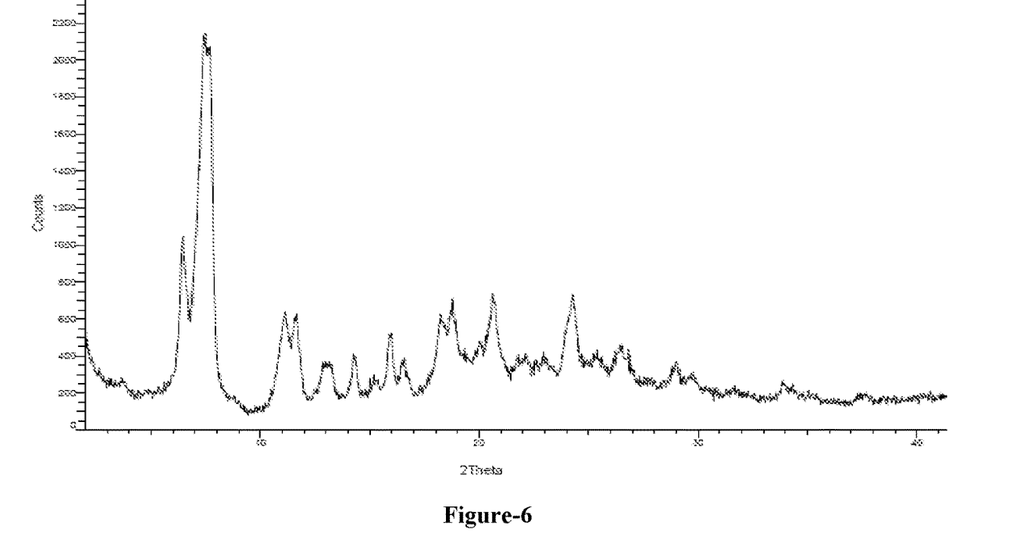
FIG. 6: Illustrates the PXRD pattern of crystalline form-L of compound of formula-1a obtained according to example-5

In another aspect of the first embodiment of the present invention, the crystalline polymorph is further characterized by;
a) its PXRD pattern having peaks at about 7.4, 7.6, 11.1, 15.9, 18.2, 18.7, 20.6 and 24.2±0.2° of 2-theta, and/or
b) its PXRD pattern as illustrated in FIG. 6.

Figure 7:
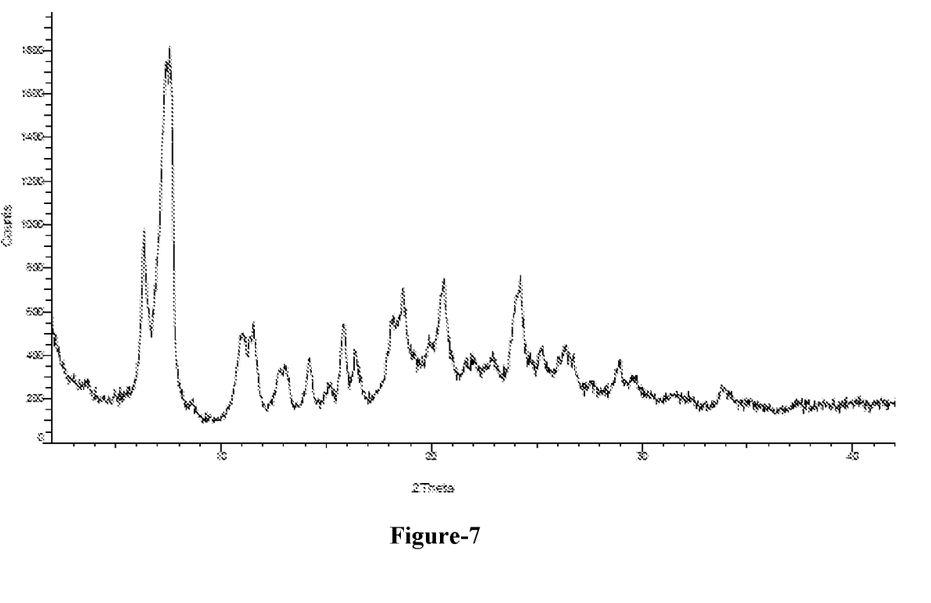
FIG. 7: Illustrates the PXRD pattern of crystalline form-L of compound of formula-1a obtained according to example-6.

In another aspect of the first embodiment of the present invention, the crystalline polymorph is further characterized by;
a) its PXRD pattern having peaks at about 7.4, 7.6, 11.1, 15.9, 18.2, 18.7, 20.6 and 24.2±0.2° of 2-theta, and/or
b) its PXRD pattern as illustrated in FIG. 7.

The second embodiment of the present invention provides a process for the preparation of crystalline polymorph of compound of formula-1a characterized by its PXRD pattern having peaks at about 6.4, 11.6, 14.2 and 16.5±0.2° of 2θ, comprising;
a) providing a mixture of compound of formula-1a and a solvent or mixture of solvents at a suitable temperature,
b) obtaining the crystalline polymorph of compound of formula-1a characterized by its PXRD pattern having peaks at about 6.4, 11.6, 14.2 and 16.5±0.2° of 2θ.

The solvent is selected from alcohol solvents, polar solvents, ester solvents, ether solvents, nitrile solvents, ketone solvents, hydrocarbon solvents, polar aprotic solvents or mixtures thereof.

In an embodiment of the present invention, the solvent is preferably selected from alcohol solvents, polar solvents such as water or mixture thereof.

In a more preferred embodiment the solvent is a mixture of alcohol solvent(s) and water.

The suitable temperature ranges from about −40° C. to about 100° C.

In the above process, the obtained crystalline polymorph can be isolated from the reaction mixture and the isolation can be carried out by removing the solvent using techniques such as filtration, evaporation, distillation optionally under reduced pressure, decantation and crystallization. Isolation can be done by any other methods known in the art.

In one embodiment of the present invention, the said process further comprises adding seed material to the reaction mixture.

In an embodiment of the present invention, the crystalline polymorph obtained is dried at a suitable temperature ranges from about 25° C. to about 120° C. for about 30 min to about 20 hr.

The third embodiment of the present invention provides novel crystalline polymorph of compound of formula-1a and process for its preparation. The said novel crystalline polymorph is herein after designated as crystalline form-S.

The crystalline form-S of compound of formula-1a of the present invention is characterized by its PXRD pattern having peak at about 7.7±0.2° of 2θ.

The crystalline form-S of compound of formula-1a is further characterized by its PXRD pattern having peaks at about 6.4, 11.6 and 14.2±0.2° of 2θ.

In another embodiment, the crystalline form-S of compound of formula-1a is further characterized by its PXRD pattern having peaks at about 12.8, 13.2, 15.2, 15.9, 16.5, 18.3, 18.6, 19.9, 20.6, 24.2, 25.3, 26.4, 28.9 and 29.7±0.2° of 2θ.

The crystalline form-S of compound of formula-1a of the present invention is further characterized by its PXRD pattern as illustrated in FIG. 1.

The fourth embodiment of the present invention provides a process for the preparation of crystalline form-S of compound of formula-1a, comprising;
a) providing a mixture of compound of formula-1a and a solvent or mixture of solvents at a suitable temperature,
b) obtaining crystalline form-S of compound of formula-1a.

The solvent is selected from alcohol solvents, polar solvents, ester solvents, ether solvents, nitrile solvents, ketone solvents, hydrocarbon solvents, polar aprotic solvents or mixtures thereof.

In an embodiment of the present invention, the solvent is preferably selected from alcohol solvents, polar solvents such as water or mixture thereof.

In a more preferred embodiment the solvent is a mixture of alcohol solvent(s) and water.

The suitable temperature ranges from about −40° C. to about 100° C.

In the above process, the obtained crystalline polymorph can be isolated from the reaction mixture and the isolation can be carried out by removing the solvent using techniques such as filtration, evaporation, distillation optionally under reduced pressure, decantation and crystallization. Isolation can be done by any other methods known in the art.

In one embodiment of the present invention, the said process further comprises adding seed material to the reaction mixture.

In an embodiment of the present invention the crystalline form-S obtained is dried at a suitable temperature ranges from about 25° C. to about 120° C. for about 30 min to about 20 hr.

The fifth embodiment of the present invention provides a process for the preparation of crystalline form-S of compound of formula-1a, comprising;
 a) treating (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-ol compound of formula-1 with a sodium source in a solvent or mixture of solvents,
 b) obtaining crystalline form-S of compound of formula-1a.

The temperature in step-a) ranges from about −10° C. to reflux temperature of the solvent used; sodium source is selected from sodium hydride, sodium hydroxide, sodium alkoxide, sodium carbonate, sodium bicarbonate or any other sodium source; wherein the said sodium source is optionally dissolved in a solvent; the solvent is selected from alcohol solvents, ester solvents, ether solvents, nitrile solvents, ketone solvents, hydrocarbon solvents, polar aprotic solvents, polar solvents or mixtures thereof.

In a preferred embodiment, the sodium source is sodium hydroxide and the solvent is a mixture of alcohol(s) and water.

In one variant of process for the preparation of form-S, the compound of formula-1 is treated with a solution of sodium source in a solvent or mixture of solvents wherein the solvent is selected from those defined above in fifth embodiment.

The sixth embodiment of the present invention provides a process for preparation of crystalline form-S of compound of formula-1a, comprising;
 a) treating compound of formula-1 with a solution of sodium hydroxide in a mixture of methanol, water and isopropanol,
 b) obtaining crystalline form-S of compound of formula-1a.

The solution of sodium hydroxide in step a) is prepared by dissolving sodium hydroxide in a mixture of methanol and water and the obtained solution is combined with isopropanol at a suitable temperature. The suitable temperature ranges from about −10° C. to about reflux temperature of the solvent used.

Isolation of crystalline form-S from the reaction mixture can be carried out by any of the techniques mentioned above or it can be done by conventional methods known in the art.

The seventh embodiment of the present invention provides a novel crystalline polymorph of compound of formula-1a and process for its preparation. The said novel crystalline polymorph is herein after designated as crystalline form-N.

The crystalline form-N of compound of formula-1a of the present invention is characterized by its PXRD pattern having peak at about 6.9±0.2° of 2θ.

The crystalline form-N of compound of formula-1a is further characterized by its PXRD pattern having peaks at about 10.7, 13.1 and 20.8±0.2° of 2θ.

Figure 2:
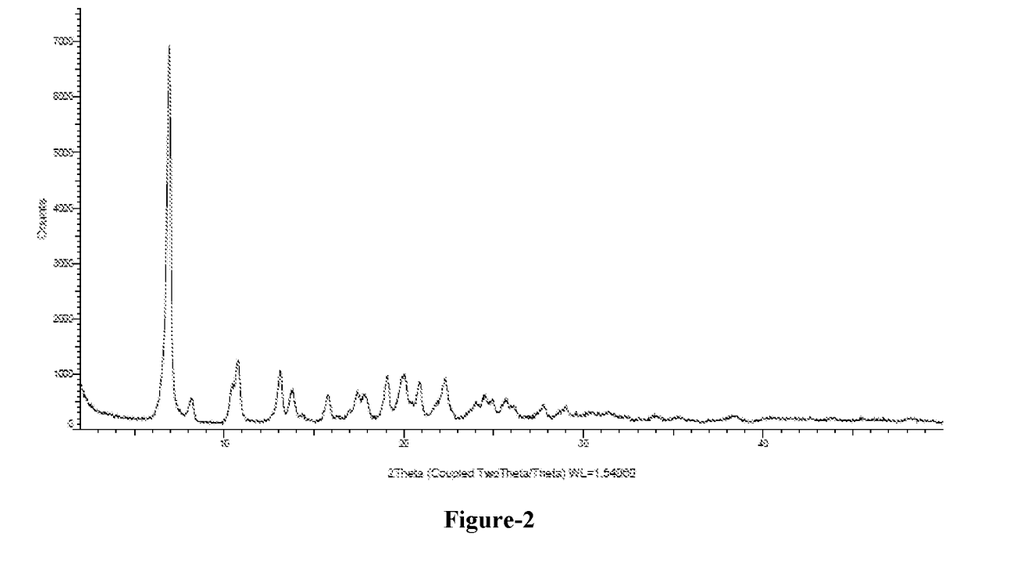

The crystalline form-N of compound of formula-1a of the present invention is further characterized by its PXRD pattern as illustrated in FIG. 2.

The eighth embodiment of the present invention provides a process for the preparation of crystalline form-N of compound of formula-1a, comprising:
 a) treating compound of formula-1 with a sodium source in a suitable solvent or mixture of solvents,
 b) obtaining crystalline form-N of compound of formula-1a.

The suitable temperature in step-a) ranges from about −10° C. to about reflux temperature of the solvent used; the sodium source and solvent are same as defined in fifth embodiment of the present invention.

The isolation can be carried out by removing the solvent using the techniques such as filtration or distillation or vacuum distillation or decantation from the mixture, crystallization or recrystallization from suitable solvent selected from the solvents defined hereinbefore or by using suitable anti-solvent which is selected from ester solvents, ether solvents, ketone solvents or hydrocarbon solvents, chloro solvents, nitrile solvents or mixtures thereof or isolation can be done by any other methods known in the art.

Figure 3:
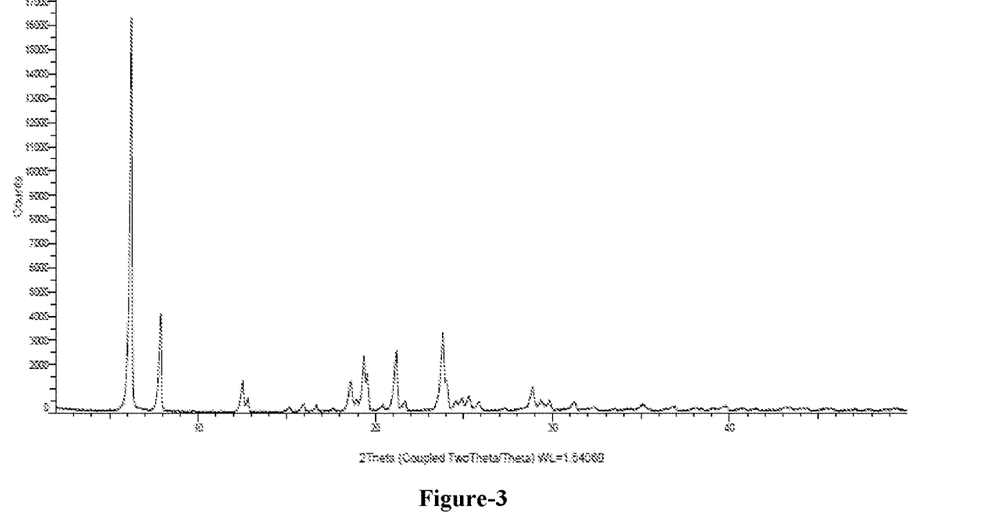

The ninth embodiment of the present invention provides crystalline 1,3-butane diol solvate of compound of formula-1a and process for its preparation. The said crystalline 1,3-butane diol solvate of compound of formula-1a of the present invention is characterized by its PXRD pattern as illustrated in FIG. 3.

The tenth embodiment of the present invention provides a process for preparation of crystalline 1,3-butanediol solvate of compound of formula-1a, comprising;
 a) treating compound of formula-1 with a sodium source in 1,3-butane diol at a suitable temperature,
 b) obtaining crystalline 1,3-butanediol solvate of compound of formula-1a.

The temperature in step-a) ranges from about 0° C. to about reflux temperature of the solvent used; the sodium source is selected from sodium hydride, sodium hydroxide, sodium alkoxide, sodium carbonate, sodium bicarbonate or any other suitable sodium source; wherein the said sodium source is optionally dissolved in a solvent; the solvent is selected from alcohol solvents, ester solvents, ether solvents, nitrile solvents, ketone solvents, hydrocarbon solvents, polar-aprotic solvents, polar solvents or mixtures thereof.

Figure 4:
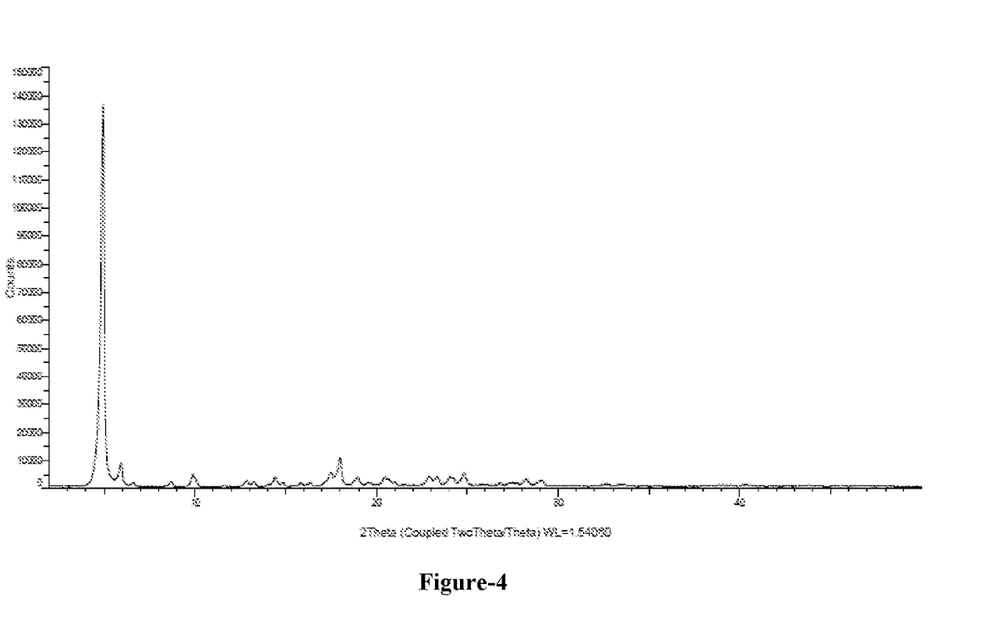

The eleventh embodiment of the present invention provides crystalline benzyl alcohol solvate of compound of formula-1a and process for its preparation. The said crystalline benzyl alcohol solvate of compound of formula-1a of the present invention is characterized by its PXRD pattern as illustrated in FIG. 4.

The twelfth embodiment of the present invention provides a process for the preparation of crystalline benzyl alcohol solvate of compound of formula-1a, comprising;
 a) adding benzyl alcohol to compound of formula-1a,
 b) optionally heating the reaction mixture to a suitable temperature,
 c) adding a solvent or mixture of solvents to the above reaction mixture,
 d) obtaining crystalline benzyl alcohol solvate of compound of formula-1a.

The temperature in step b) ranges from about 0° C. to about reflux temperature of the solvent used;

The solvent in step c) is selected from alcohol solvents, ester solvents, ether solvents, nitrile solvents, ketone solvents, hydrocarbon solvents, polar aprotic solvents, polar solvents or mixtures thereof.

The isolation can be carried out by removing the solvent using the techniques such as filtration or distillation or vacuum distillation or decantation from the mixture, crystallization or recrystallization from suitable solvent selected from the solvents defined hereinbefore or by using suitable anti-solvent which is selected from ester solvents, ether solvents, ketone solvents or hydrocarbon solvents, chloro solvents, nitrile solvents or mixtures thereof or isolation can be done by any other methods known in the art.

In the present invention, the solvent may be removed optionally under reduced pressures, at temperatures less than about 200° C., less than about 150° C., less than about 100° C., less than about 60° C., less than about 40° C., less than about 20° C., less than about 0° C., less than about −20° C., less than about −40° C. or less than about −60° C.

The thirteenth embodiment of the present invention provides a novel crystalline polymorph of compound of formula-1a, which is herein after designated as crystalline form-L.

The crystalline form-L of compound of formula-1a of the present invention is characterized by its PXRD pattern having peaks at about 7.4 and 7.6±0.2° of 2-theta.

The crystalline form-L of compound of formula-1a of the present invention is further characterized by its PXRD pattern having peaks at about 6.4, 11.6, 14.2 and 16.5±0.2° of 2-theta.

The crystalline form-L of compound of formula-1a of the present invention is further characterized by its PXRD pattern having peaks at about 11.1, 15.9, 18.2, 18.7, 20.6 and 24.2±0.2° of 2-theta.

In one aspect of the present invention, the crystalline form-L is characterized by its PXRD pattern as illustrated in FIG. 6.

In another aspect of the present invention, the crystalline form-L is characterized by its PXRD pattern as illustrated in FIG. 7.

The fourteenth embodiment of the present invention provides a process for the preparation of crystalline form-L of compound of formula-1a, comprising;
  a) providing a mixture of compound of formula-1a and a solvent or mixture of solvents at a suitable temperature,
  b) obtaining crystalline form-L of compound of formula-1a.

Wherein, the solvent is selected from alcohol solvents, polar solvents, ester solvents, ether solvents, nitrile solvents, ketone solvents, hydrocarbon solvents, polar aprotic solvents or mixtures thereof.

In an embodiment of the present invention, the solvent is preferably selected from alcohol solvents, polar solvents such as water or mixture thereof.

In a more preferred embodiment the solvent is a mixture of alcohol solvent(s) and water.

The suitable temperature ranges from about −40° C. to about 100° C.

The crystalline form-L obtained by the processes of the present invention can be isolated from the reaction mixture and the isolation can be carried out by removing the solvent using techniques such as filtration, evaporation, distillation optionally under reduced pressure, decantation and crystallization. Isolation can be done by any other methods known in the art.

In one embodiment of the present invention, the said process further comprises adding seed material to the reaction mixture.

In an embodiment of the present invention the crystalline polymorph obtained is dried at a suitable temperature ranges from about 25° C. to about 120° C. for about 30 min to about 20 hr.

The fifteenth embodiment of the present invention provides a process for the preparation of crystalline form-L of compound of formula-1a, comprising;
  a) treating compound of formula-1 with a sodium source in a solvent or mixture of solvents,
  b) obtaining crystalline form-L of compound of formula-1a.

The temperature in step-a) ranges from about −10° C. to reflux temperature of the solvent used; sodium source is selected from sodium hydride, sodium hydroxide, sodium alkoxides, sodium carbonate, sodium bicarbonate or any other sodium source; wherein the said sodium source is optionally dissolved in a solvent; the solvent is selected from alcohol solvents, ester solvents, ether solvents, nitrile solvents, ketone solvents, hydrocarbon solvents, polar aprotic solvents, polar solvents or mixtures thereof.

In a preferred embodiment, the sodium source is sodium hydroxide and the solvent is a mixture of alcohol(s) and water.

In one variant of process for the preparation of form-L, a solution of compound of formula-1 in a solvent or mixture of solvents is treated with a solution of sodium source in a solvent or mixture of solvents.

Wherein, the solvent is selected from alcohol solvents, polar solvents such as water or mixtures thereof.

The sixteenth embodiment of the present invention provides a process for the preparation of crystalline form-L of compound of formula-1a, comprising;
  a) providing a solution of compound of formula-1 in a solvent or mixture of solvents at a suitable temperature,
  b) combining the solution with a solution of sodium hydroxide in a solvent or mixture of solvents at a suitable temperature,
  c) obtaining crystalline form-L of compound of formula-1a.

Wherein, the solvent in step-a) and step-b) is selected from alcohol solvents, polar solvents such as water, ester solvents, ether solvents, nitrile solvents, ketone solvents, hydrocarbon solvents, polar aprotic solvents or mixtures thereof.

The suitable temperature ranges from about −40° C. to about 100° C.

In an embodiment the solvent in step-a) and step-b) is selected from alcohol solvents, polar solvents or mixtures thereof;

In a preferred embodiment, the solvent in step-a) is a mixture of methanol and water and the solvent in step-b) is isopropyl alcohol.

In step-a) a solution of compound of formula-1 in a solvent can be obtained by dissolving compound of formula-1 in the said solvent at a suitable temperature ranging from 25° C. to reflux temperature of the solvent used; and the solvent can be selected from alcohol solvents, polar solvents such as water or mixtures thereof;

The suitable temperature ranges from −40° C. to 80° C.;

In step-b) providing a solution of sodium hydroxide in a solvent at a suitable temperature can be carried out by dissolving sodium hydroxide in the said solvent at a temperature ranging from 25° C. to 80° C. and optionally cooling the obtained solution to a temperature ranging from −40° C. to 20° C.

In one embodiment of the present invention, the said process further comprises adding seed material to the solution of step-a) or to a solution of sodium hydroxide in a solvent utilized in step-b).

The seventeenth embodiment of the present invention provides a process for the preparation of crystalline form-L of compound of formula-1a, comprising;
 a) providing a solution of sodium hydroxide in isopropyl alcohol at a suitable temperature,
 b) combining the solution with a solution of compound of formula-1 in a mixture of methanol and water at a suitable temperature,
 c) filtering the solid,
 d) drying the solid at a suitable temperature to provide crystalline form-L of compound of formula-1a.

The suitable temperature in step-a) and step-b) ranges from −40° C. to 100° C.

Figure 5:
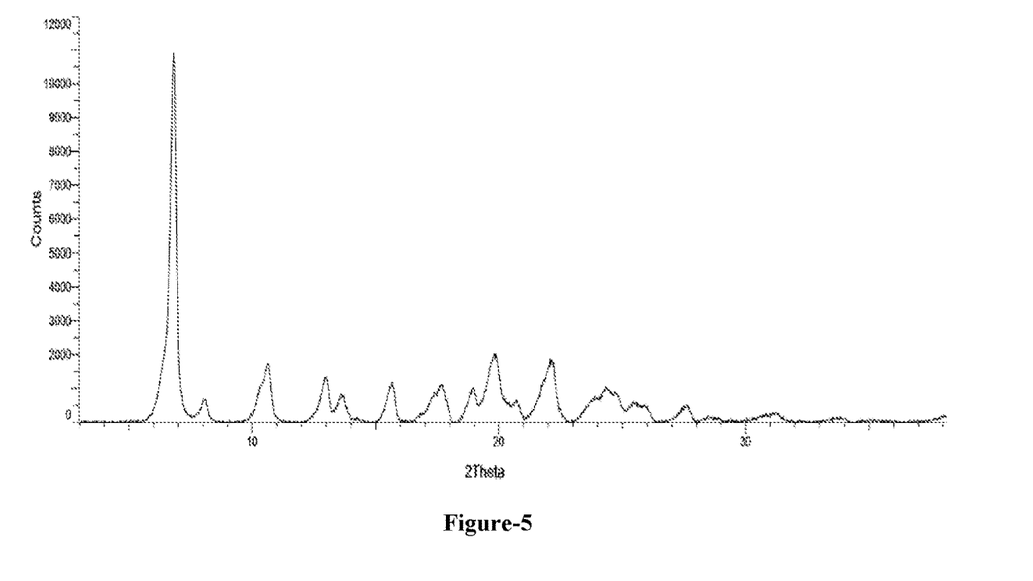

In one embodiment of the present invention, a small amount of crystals having PXRD pattern as shown in FIG. 5 can be added as seed material to a solution of step-a) or to a solution of compound of formula-1 utilized in step-b).

In another embodiment of the present invention, a small amount of crystalline form-L can be added as seed material to a solution of step-a) or to a solution of compound of formula-1 utilized in step-b).

In an embodiment of the present invention, the solid obtained in step-c) has PXRD pattern as illustrated in FIG. 5.

The compound of formula-1 and compound of formula-1a which are used in the present invention can be prepared by any of the processes known in the art.

In the above processes, any polymorphic form of compound of formula-1 or compound of formula-1a viz., crystalline form or amorphous form can be used as input for the preparation of various polymorphs of the present invention.

The crystalline forms of compound of formula-1a or its solvates of the present invention are useful as input for the preparation of other polymorphic forms of compound of formula-1a viz., crystalline polymorphs as well as amorphous form of compound of formula-1a.

An embodiment of the present invention provides the use of any of the crystalline forms of compound of formula-1a of the present invention for the preparation of pharmaceutical formulations.

The other embodiment of the present invention provides a pharmaceutical composition comprising any of the crystalline forms of compound of formula-1a of the present invention and at least one pharmaceutically acceptable excipient, which is used for the treatment of human immunodeficiency virus (HIV) infection in combination with other antiretroviral agents.

The another embodiment of the present invention provides a method of treating a patient in need thereof comprising administering to the said patient a therapeutically effective amount of any of the crystalline forms of compound of formula-1a of the present invention.

The crystalline forms of compound of formula-1a or its solvates of the present invention are useful and suitable for the preparation of various pharmaceutical compositions formulated in a manner suitable for the route of administration to be used where at least a portion of compound of formula-1a is present in the composition in particular polymorphic form mentioned. Such pharmaceutical compositions may comprise compound of formula-1a present in the composition in a range of between 0.005% and 100% (wt/wt), with the balance of the pharmaceutical composition comprising additional substances such as excipients, diluents, lubricants, binders, wetting agents, disintegrating agents, glidants, sweetening agents, flavoring agents, emulsifying agents, solubilizing agents, pH buffering agents, perfuming agents, surface stabilizing agents, suspending agents and other conventional pharmaceutically inactive agents.

An embodiment of the present invention provides compound of formula-1a having particle size distribution of D90 less than 500 µm, preferably less than 400 µm, more preferably less than 300 µm, most preferably less than 200 µm.

Another embodiment of the present invention provides compound of formula-1a having particle size distribution of D90 less than about 100 µm, preferably less than about 50 µm, more preferably less than about 20 µm, most preferably less than about 10 µm.

The compound of formula-1a obtained by the process of the present invention can be further micronized or milled to get desired particle size to achieve desired solubility profile based on different forms of pharmaceutical composition requirements. Techniques that may be used for particle size reduction includes but not limited to single or multi-stage micronization using cutting mills, pin/cage mills, hammer mills, jet mills, fluidized bed jet mills, ball mills and roller mills. Milling/micronization may be performed before drying or after drying of the product.

P-XRD Method of Analysis:

The PXRD analysis of compound of formula-1a of the present invention was carried out using BRUKER/D8 ADVANCE diffractometer using CuKα radiation of wavelength 1.5406A° and at a continuous scan speed of 0.03°/min.

It is known in the art that powder X-ray diffraction pattern (P-XRD or PXRD) may be obtained which has one or more measurement errors depending on measurement conditions (such as equipment, sample preparation or machine used). In particular, it is generally known that intensities in an powder X-ray diffraction pattern may fluctuate depending on measurement conditions and sample preparation. For example, persons skilled in the art of powder X-ray diffraction will realize that the relative intensities of the peaks may vary according to the orientation of the sample under test and on the type and setting of the instrument used. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a powder diffraction pattern substantially identical to those disclosed herein fall within the scope of the present disclosure.

Generally, a measurement error of a diffraction angle in an powder X-ray diffraction pattern is typically ±0.2° of 2-theta.

The best mode of carrying out the present invention is illustrated by the below mentioned examples. These examples are provided as illustration only and hence should not be construed as limitation to the scope of the invention.

EXAMPLES

Example-1: Preparation of Crystalline Form-S of Compound of Formula-1a

Sodium hydroxide (0.572 gm) is dissolved in a mixture of water and methanol (60 ml) at 25-30° C. The obtained solution is added to pre-cooled isopropyl alcohol (200 ml) at 0-5° C. 5.0 gm of compound of formula-1 is added to the above reaction mixture at 0-5° C. Stirred the reaction mixture for 36 hr at the same temperature. Filtered the solid and dried the material at 120° C. to get the title compound. The PXRD pattern of the obtained compound is illustrated in FIG. 1.

Yield: 4.0 gm.

Example-2: Preparation of Crystalline Form-N of Compound of Formula-1a

Sodium hydroxide (0.572 gm) is dissolved in a mixture of water and methanol (60 ml) at 25-30° C. The obtained solution is added to pre-cooled isopropyl alcohol (200 ml) at 0-5° C. 5.0 gm of compound of formula-1 is added to the above reaction mixture at 0-5° C. Stirred the reaction mixture for 36 hr at the same temperature. Filtered the solid and dried the material at 40 to 45° C. to get the title compound. The PXRD pattern of the obtained compound is illustrated in FIG. 2.

Yield: 4.2 gm.

Example-3: Preparation of Crystalline 1,3-Butane Diol Solvate of Compound of Formula-1a 10 gm of compound of formula-1 is added to 1,3-butane diol (200 ml) at 25-30° C. and heat the reaction mixture to 40-45° C. Stirred the reaction mixture for 2 hr and added a solution of sodium hydroxide dissolved in dimethylsulfoxide to it at the same temperature. Stirred the reaction mixture for 3 hr at 40-45° C. Filtered the solid and dried the material to get the title compound. The PXRD pattern of the obtained compound is illustrated in FIG. 3. Yield: 12.0 gm.

Example-4: Preparation of Crystalline Benzyl Alcohol Solvate of Compound of Formula-1a 100 ml of benzyl alcohol is added to 5 gm of compound of formula-1a at 25-30° C. and stirred for 30 min at the same temperature. Methyl tertiary butyl ether (300 ml) is added to the above reaction mixture and stirred for 2 hr at 25-30° C. Filtered the solid and dried the material to get the title compound.

The PXRD pattern of the obtained compound is illustrated in FIG. 4.

Yield: 4.5 gm.

Example-5: Preparation of Crystalline Form-L of Compound of Formula-1a

A mixture of sodium hydroxide (8.01 gm) and isopropyl alcohol (4.9 Lt) was heated to 55-60° C. and stirred for 15 min at the same temperature. Cooled the reaction mixture to −20° C. to −15° C. and stirred for 5 min at the same temperature. Seeding material (3.5 gm) was added to the reaction mixture at −20° C. to −15° C. A pre-heated (55-60° C.) solution of compound of formula-1 (70 gm) in methanol (3.5 Lt) and water (350 ml) was slowly added to the reaction mixture at −20° C. to −15° C. Raised the temperature of the reaction mixture to −10° C. to −5° C. and stirred for 3 hr at the same temperature. Filtered the solid and suck dried.

The PXRD pattern of the obtained compound is shown in FIG. 5.

Yield: 75.0 gm.

Further dried the compound at 95-100° C. for 4-5 hr to get the title compound.

The PXRD pattern of the obtained compound is shown in FIG. 6.

Yield: 51.0 gm.

Example-6: Preparation of Crystalline Form-L of Compound of Formula-1a

A mixture of sodium hydroxide (5.72 gm) and isopropyl alcohol (3.5 Lt) was heated to 55-60° C. and stirred for 15 min at the same temperature. Cooled the reaction mixture to −20° C. to −15° C. and stirred for 10 min at the same temperature. Seeding material (2.5 gm) was added to the reaction mixture at −20° C. to −15° C. A pre-heated (55-60° C.) solution of compound of formula-1 (50 gm) in methanol (2.5 Lt) and water (250 ml) was slowly added to the reaction mixture at −20° C. to −15° C. Raised the temperature of the reaction mixture to −10° C. to −5° C. and stirred for 3 hr at the same temperature. Filtered the solid and suck dried.

The PXRD pattern of the obtained compound is similar to FIG. 5.

Yield: 60.0 gm.

Further dried the obtained compound at 95-100° C. for 4-5 hr to get the title compound.

The PXRD pattern of the obtained compound is shown in FIG. 7.

Yield: 40.0 gm.

Example-7: Preparation of Crystalline Form-L of Compound of Formula-1a

Step-a): A mixture of sodium hydroxide (5.72 gm) and isopropyl alcohol (3.5 Lt) was heated to 55-60° C. and stirred for 45 min at the same temperature. Cooled the reaction mixture to −15° C. to −10° C. and stirred for 10 min at the same temperature. Seeding material (2.5 gm) was added to the reaction mixture at −15° C. to −10° C.

Step-b): Methanol (2.5 Lt) was added to compound of formula-1 (50 gm) at 25-30° C. Heated the reaction mixture to 55-60° C. and stirred for 15 min at the same temperature. Water (250 ml) was added to the reaction mixture at 55-60° C. Filtered the solution to make it particle free. The obtained filtrate was slowly added to the reaction mixture obtained in step-a) at −15° C. to −10° C. Slowly raised the temperature of the reaction mixture to −10° C. to −5° C. and stirred for 4 hr at the same temperature. Filtered the solid and suck dried.

The PXRD pattern of the obtained compound is similar to FIG. 5.

Yield: 52.0 gm.

Further dried the compound at 95-100° C. for 5 hr to get the title compound.

The PXRD pattern of the obtained compound is similar to FIG. 7.

Yield: 40.0 gm.

We claim:

1. Crystalline polymorph of sodium (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate compound of formula-1a characterized by its PXRD pattern having peaks at 6.4, 11.6, 14.2 and 16.5±0.2° of 2θ.

2. A process for the preparation of crystalline polymorph of compound of formula-1a of claim 1, comprising;
    a) providing a mixture of compound of formula-1a and a solvent or mixture of solvents at a suitable temperature,
    b) obtaining the crystalline polymorph of compound of formula-1a of claim 1.

3. The process according to claim 2, wherein the solvent is selected from alcohol solvents, polar solvents, ester solvents, ether solvents, nitrile solvents, ketone solvents, hydrocarbon solvents, polar aprotic solvents or mixtures thereof; and the temperature ranges from −40° C. to 100° C.

4. A crystalline polymorph of compound of formula-1a according to claim 1, which is further characterized by;
   a) its PXRD pattern having peaks at 7.7, 12.8, 13.2, 15.2, 15.9, 18.3, 18.6, 19.9, 20.6, 24.2, 25.3, 26.4, 28.9 and 29.7±0.2° of 2θ, and/or
   b) its PXRD pattern as illustrated in FIG. 1.

5. A process for the preparation of crystalline polymorph of compound of formula-1a of claim 4, comprising;
   a) providing a mixture of compound of formula-1a and a solvent or mixture of solvents at a suitable temperature,
   b) obtaining crystalline polymorph of compound of formula-1a of claim 4.

6. The process according to claim 5, wherein the solvent is selected from alcohol solvents, polar solvents, ester solvents, ether solvents, nitrile solvents, ketone solvents, hydrocarbon solvents, polar aprotic solvents or mixtures thereof and the temperature ranges from −40° C. to 100° C.

7. A process for the preparation of crystalline polymorph of compound of formula-1a of claim 4, comprising;
   a) treating (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-ol compound of formula-1 with a sodium source in a solvent or mixture of solvents,
   b) obtaining crystalline polymorph of compound of formula-1a of claim 4.

8. The process according to claim 7, wherein,
   the sodium source is selected from sodium hydride, sodium hydroxide, sodium alkoxide, sodium carbonate, sodium bicarbonate;
   the solvent is selected from alcohol solvents, ester solvents, ether solvents, nitrile solvents, ketone solvents, hydrocarbon solvents, polar aprotic solvents, polar solvents or mixtures thereof.

9. A crystalline polymorph of compound of formula-1a according to claim 1, which is further characterized by;
   a) its PXRD pattern having peaks at 7.4, 7.6, 11.1, 15.9, 18.2, 18.7, 20.6 and 24.2±0.2° of 2-theta, and/or
   b) its PXRD pattern as illustrated in FIG. 6.

10. A crystalline polymorph of compound of formula-1a according to claim 1, which is further characterized by;
    a) its PXRD pattern having peaks at 7.4, 7.6, 11.1, 15.9, 18.2, 18.7, 20.6 and 24.2±0.2° of 2-theta, and/or
    b) its PXRD pattern as illustrated in FIG. 7.

11. A process for the preparation of crystalline polymorph of compound of formula-1a according to claim 9, comprising:
    a) providing a mixture of compound of formula-1a and a solvent or mixture of solvents at a suitable temperature,
    b) obtaining crystalline polymorph of compound of formula-1a.

12. The process according to claim 11, wherein the solvent is selected from alcohol solvents, polar solvents, ester solvents, ether solvents, nitrile solvents, ketone solvents, hydrocarbon solvents, polar aprotic solvents or mixtures thereof and the suitable temperature ranges from −40° C. to 100° C.

13. A process for the preparation of crystalline polymorph of compound of formula-1a of claim 9, comprising;
    a) treating (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-ol compound of formula-1 with a sodium source in a solvent or mixture of solvents,
    b) obtaining crystalline polymorph of compound of formula-1a of claim 9 or claim 10.

14. The process according to claim 13, wherein,
    the sodium source is selected from sodium hydride, sodium hydroxide, sodium alkoxides, sodium carbonate, sodium bicarbonate; and
    the solvent is selected from alcohol solvents, ester solvents, ether solvents, nitrile solvents, ketone solvents, hydrocarbon solvents, polar aprotic solvents, polar solvents or mixtures thereof.

15. A pharmaceutical composition comprising crystalline polymorph of compound of formula-1a of claim 1 and at least one pharmaceutically acceptable excipient.

16. A method of treating a human immunodeficiency virus type 1 (HIV-1) infection in a subject comprising administering to the subject in need thereof a therapeutically effective amount of the compound according to claim 1.

* * * * *